(12) United States Patent
Nishimura et al.

(10) Patent No.: US 11,906,407 B2
(45) Date of Patent: Feb. 20, 2024

(54) FLOW ANALYSIS DEVICE AND FLOW ANALYSIS METHOD

(71) Applicant: BL TEC K.K., Osaka (JP)

(72) Inventors: Takashi Nishimura, Tokyo (JP); Kazuo Masaki, Tokyo (JP)

(73) Assignee: BL TEC K.K., Osaka (JP)

(*) Notice: Subject to any disclaimer, the term of this patent is extended or adjusted under 35 U.S.C. 154(b) by 0 days.

(21) Appl. No.: 17/788,521

(22) PCT Filed: Mar. 31, 2021

(86) PCT No.: PCT/JP2021/013789
§ 371 (c)(1),
(2) Date: Jun. 23, 2022

(87) PCT Pub. No.: WO2021/205953
PCT Pub. Date: Oct. 14, 2021

(65) Prior Publication Data
US 2023/0038524 A1    Feb. 9, 2023

(30) Foreign Application Priority Data

Apr. 8, 2020 (JP) .................. 2020-070024

(51) Int. Cl.
*G01N 1/38* (2006.01)
*G01N 15/06* (2006.01)
*G01N 15/00* (2006.01)

(52) U.S. Cl.
CPC .............. *G01N 1/38* (2013.01); *G01N 15/06* (2013.01); *G01N 15/0656* (2013.01);
(Continued)

(58) Field of Classification Search
CPC ...... G01N 1/38; G01N 15/06; G01N 15/0656; G01N 2015/0053; G01N 2015/0681; G01N 2015/0687; G01N 2015/0693
See application file for complete search history.

(56) References Cited

U.S. PATENT DOCUMENTS 4,476,981 A * 10/1984 Yoshida ................. B07C 5/361
209/653
4,804,519 A    2/1989 Sainz et al.
(Continued)

FOREIGN PATENT DOCUMENTS

CA    2160235    10/1994
CN    108603834    9/2018
(Continued)

OTHER PUBLICATIONS

1st Office Action for TW110112154 dated Dec. 13, 2021, 6 pages.
(Continued)

*Primary Examiner* — Tri T Ton
*Assistant Examiner* — Jarreas Underwood
(74) *Attorney, Agent, or Firm* — Casimir Jones, S.C.; Robert A. Goetz (57) ABSTRACT

Provided is a flow analyzer and a flow analysis method each of which makes it possible to stably and continuously measure a sample. The flow analyzer and the flow analysis method each include: a marker introducing device (2) which is for introducing a marker into a tube (3); and a marker detecting device (5) which detects the marker and outputs a detection signal to an analyzing device (4), the analyzing device (4) acquiring analysis data on the basis of the detection signal.

12 Claims, 4 Drawing Sheets

(52) U.S. Cl.
CPC ........... *G01N 2015/0053* (2013.01); *G01N 2015/0681* (2013.01); *G01N 2015/0687* (2013.01); *G01N 2015/0693* (2013.01)

(56) References Cited

U.S. PATENT DOCUMENTS

| | | | |
|---|---|---|---|
| 5,407,832 A * | 4/1995 | Hayashibe | G01N 33/84 436/171 |
| 7,897,032 B2 | 3/2011 | Viltchinskaia et al. | |
| 2004/0248307 A1* | 12/2004 | Grof | G01N 33/2882 422/62 |
| 2006/0097144 A1* | 5/2006 | Kingston | H01J 49/04 250/282 |
| 2006/0104827 A1 | 5/2006 | Shaw et al. | |
| 2009/0117664 A1* | 5/2009 | Shinoda | G01N 35/08 209/39 |
| 2011/0101215 A1* | 5/2011 | Hirabayashi | G01N 30/8675 250/281 |
| 2012/0153143 A1* | 6/2012 | Kennedy | H01J 49/165 250/288 |
| 2014/0212882 A1* | 7/2014 | Handique | B01L 3/502738 435/6.12 |
| 2016/0172178 A1* | 6/2016 | Apffel | G01N 15/1459 250/336.1 |
| 2018/0270465 A1* | 9/2018 | Bendall | G01N 21/954 |
| 2018/0276811 A1* | 9/2018 | Wen | G01N 21/8851 |
| 2018/0364160 A1 | 12/2018 | Aben et al. | |
| 2019/0222810 A1* | 7/2019 | Horiguchi | G06T 7/0004 |
| 2021/0048395 A1* | 2/2021 | Will | H04N 7/188 |
| 2023/0038524 A1* | 2/2023 | Nishimura | G01N 1/38 |

FOREIGN PATENT DOCUMENTS

| | | |
|---|---|---|
| CN | 202180009468.5 | 7/2023 |
| JP | 59/501994 | 11/1984 |
| JP | 06-222005 | 8/1994 |
| JP | 06-249783 | 9/1994 |
| JP | 08-136551 | 5/1996 |
| JP | 2004-526952 | 9/2004 |
| JP | 2009-288228 | 12/2009 |
| JP | 2012-530903 | 12/2012 |
| JP | 5158111 | 3/2013 |
| JP | 2019-113357 | 7/2019 |
| JP | 2020-134519 | 8/2020 |
| TW | 201908734 | 3/2019 |
| WO | WO 1984/002000 | 5/1984 |
| WO | WO 2000-67012 | 11/2000 |
| WO | WO 2009/123297 | 10/2009 |

OTHER PUBLICATIONS

Allowance for JP2021-520250 dated Aug. 31, 2021, 2 pages.
International Search Report for PCT/JP2021/013789 and its English translation dated Jun. 1, 2021, 6 pages.
Office Action For KR Patent Application No. 10-2022-7024613, dated Nov. 7, 2022, 6 pages.
Extended European Search Report for EP21784735, dated Sep. 5, 2023. 7 pages.
CN 202180009468.5, Chinese Allowance Notice, dated Jul. 25, 2023, 7 pages.

* cited by examiner

FLOW ANALYSIS DEVICE AND FLOW ANALYSIS METHOD

TECHNICAL FIELD

The present invention relates to a flow analyzer and a flow analysis method.

BACKGROUND ART

As devices for analyzing metal contained in solutions, there are atomic absorption photometers (OES), inductively coupled plasma optical emission spectrometers (ICP-OES), inductively coupled plasma mass spectrometers (ICP-MS), and the like. In order to analyze a sample with use of any of such analyzing devices, it is typically necessary to pretreat the sample, e.g., add acid and/or alkali to the sample and, as necessary, heat the sample. This pretreatment, which is carried out mainly for the purpose of decomposition of an organic matter, a suspended matter, a metal complex, and the like that coexist in a sample, is considerably time-consuming.

As a method for automating the pretreatment and thereby increasing the speed of the analysis of the sample, there is known a method in which metal ions are measured by a flow injection analysis method (FIA), which is one of flow analysis methods, in combination with an inductively coupled plasma mass spectrometer (ICP-MS) or an inductively coupled plasma optical emission spectrometer (ICP-OES) (Non-Patent Literature 1).

CITATION LIST

Non-Patent Literature

[Non-patent Literature 1]
MIYAZAKI Akira, FUJIMORI Eiji, TANAKA Atsushi, and YOSHINAGA Jun, "Purazuma bunkoho niyoru kankyoshiryo no bunseki—ICP, DCP, MIP bunseki no kiso to jitsurei—(analysis of environmental sample by plasma spectrometry—basics and practical examples of ICP, DCP, MIP analyses)", published by AGNE Gijutsu Center Inc., Feb. 20, 2020, pp. 64 to 74, pp. 198 to 240

SUMMARY OF INVENTION

Technical Problem

However, in a conventional technique as described above, a difference sometimes arises, over time, between a timing of appearance of a peak of analysis data and a timing of acquisition of the analysis data due to the viscosity and the density of a sample. Therefore, the conventional technique as described above has room for improvement in terms of stable and continuous measurement of a sample. That is, the conventional technique in which an analyzing device and a flow analysis method are combined is a technique of sequentially and continuously introducing a plurality of samples into a tube, sending them through the tube, pretreating them in the tube, and then analyzing them with use of the analyzing device. Therefore, there is a case where it is not possible to send the plurality of samples stably and uniformly in time from a point of introduction of the plurality of samples to the analyzing device. In such a case, there is a problem that, even in a case where analysis data on each of the plurality of samples is acquired from the analyzing device at regular intervals, a difference sometimes arises, over time, between a timing of appearance of a peak of the analysis data and a timing of acquisition of the analysis data.

The object of an embodiment of the present invention is to, by solving the above problem, provide a flow analyzer and a flow analysis method each of which makes it possible to stably and continuously measure a sample.

Solution to Problem

A flow analyzer in accordance with an embodiment of the present invention is a flow analyzer including: a sampling device which is for introducing a sample into a tube; and an analyzing device which analyzes the sample that is transferred through the tube, the flow analyzer further including: a marker introducing device which is for introducing a marker into the tube; and a marker detecting device which detects the marker and outputs a detection signal to the analyzing device, the analyzing device acquiring analysis data on the basis of the detection signal.

A flow analysis method in accordance with an embodiment of the present invention is a flow analysis method including: a sample introducing step of introducing a sample into a tube; and an analyzing step of analyzing the sample that is transferred through the tube, the flow analysis method further including: a marker introducing step of introducing a marker into the tube between the sample introducing step and a next sample introducing step; and a marker detecting step of detecting the marker and outputting a detection signal to an analyzing device, in the analyzing step, analysis data being acquired on the basis of the detection signal.

Advantageous Effects of Invention

According to an embodiment of the present invention, it is possible to provide a flow analyzer and a flow analysis method each of which makes it possible to stably and continuously measure a sample, by solving a problem that a difference arises between a timing of appearance of a peak of analysis data and a timing of acquisition of the analysis data.

BRIEF DESCRIPTION OF DRAWINGS

In FIG. 5, (a), (b), and (c) respectively illustrate peaks which were acquired by the marker detecting device when 60 seconds, 45 seconds, and 30 seconds were spent in introducing the rhodium into the tube.

DESCRIPTION OF EMBODIMENTS

The following description will discuss embodiments of the present invention in detail. Note, however, that the present invention is not limited to the embodiments, and can be altered within the scope of the matters described herein. The present invention also encompasses, in its technical scope, any embodiment derived by combining, as appropriate, technical means disclosed in differing embodiments.

(I) Flow Analyzer

Embodiment 1

Figure 1:
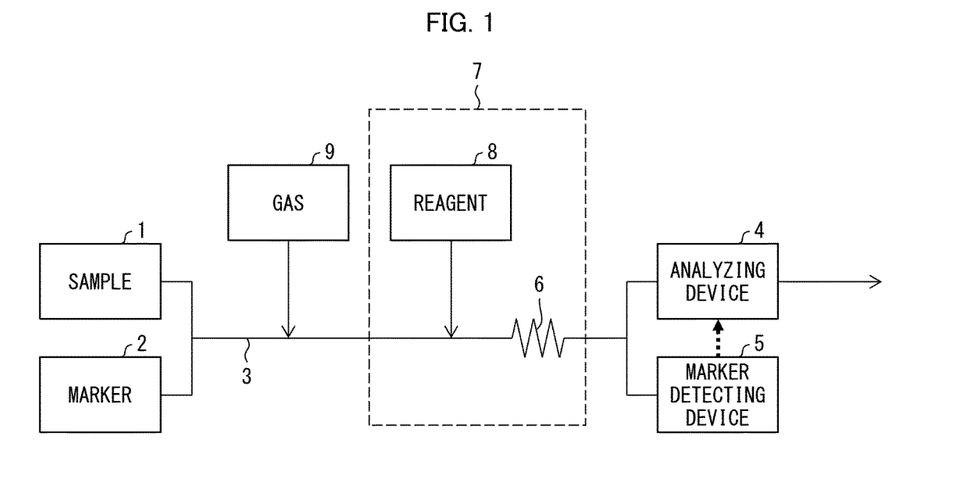
FIG. 1 is a drawing schematically illustrating a configuration of a flow analyzer in accordance with Embodiment 1 of the present invention.

An embodiment of the present invention will be described with reference to the drawings. FIG. 1 is a drawing schematically illustrating a configuration of a flow analyzer in accordance with Embodiment 1 of the present invention.

The flow analyzer in accordance with Embodiment 1 of the present invention includes: a sampling device 1 which is for introducing a sample into a tube 3; a marker introducing device 2 which is for introducing a marker into the tube 3; a gas bubble segmenting device 9 which produces, in the tube 3, a plurality of segments that are separated by gas bubbles, by carrying out gas bubble segmentation with respect to the sample and the marker that are introduced into the tube 3; a reagent adding device 8 which adds a reagent to a flow of the sample that is transferred through the tube 3; a heating device 6 which carries out a heat treatment with respect to the sample that is transferred through the tube 3; an analyzing device 4 which analyzes the sample with respect to which the heat treatment has been carried out; and a marker detecting device 5 which detects the marker and outputs a detection signal to the analyzing device 4, and the analyzing device 4 acquires analysis data on the basis of the detection signal.

The sampling device 1 is a device for sampling a sample and introducing the sample into the tube 3. In an embodiment of the present invention, the sampling device 1 includes a thief tube through which the sample is led to the tube 3 and a sampling pump which imparts a suction force to the thief tube. By the sampling pump, the sample is introduced into the tube 3 at a given flow rate. The sample is a liquid containing a substance or an element each of which is an analysis target.

The marker introducing device 2 is a device for introducing a marker into the tube 3. In an embodiment of the present invention, the marker introducing device 2 includes a thief tube through which the marker is led to the tube 3 and a pump which imparts a suction force to the thief tube. The marker only needs to contain a substance which can be detected by the marker detecting device 5, and may be the substance or may be alternatively a solution containing the substance or may be alternatively a dispersion containing the substance.

Note, here, that the marker introducing device 2 and the sampling device 1 are configured such that the marker and a given number of samples, which given number is one or more, are capable of being alternately introduced into the tube 3. That is, the introduction of the marker into the tube 3 by the marker introducing device 2 and the introduction of the given number of samples into the tube 3 by the sampling device 1 are alternately switched therebetween. This switching may be carried out manually or may be alternatively carried out automatically.

In a case where the marker introducing device 2 and the sampling device 1 are configured such that the marker and a single sample are capable of being alternately introduced into the tube 3, the marker is each time introduced into the tube 3 prior to the introduction of the single sample. For each single sample, the marker detecting device 5 detects the marker and then outputs, to the analyzing device 4, a detection signal indicative of the detection of the marker, and the analyzing device 4 acquires analysis data on the basis of the detection signal. This makes it possible to stably and continuously measure the sample, because, even in a case where it is not possible to send the sample stably and uniformly in time from a point of the introduction of the sample to the analyzing device, a difference does not arise between a timing of appearance of a peak of the analysis data and a timing of the acquisition of the analysis data.

Alternatively, in a case where the marker introducing device 2 and the sampling device 1 are configured such that the marker and two or more samples are capable of being alternately introduced into the tube 3, the marker is introduced into the tube 3 once prior to the introduction of the two or more samples. Then, the marker detecting device 5 detects the marker and then outputs, to the analyzing device 4, a detection signal indicative of the detection of the marker, and the analyzing device 4 sequentially acquires analysis data on the two or more samples on the basis of the detection signal. This makes it possible to stably and continuously measure the samples, because, even in a case where it is not possible to send the samples stably and uniformly in time from a point of the introduction of the samples to the analyzing device, a difference between a timing of appearance of a peak of the analysis data between a timing of the acquisition of the analysis data can be reduced to a certain range. The upper limit of the given number can be determined as appropriate, depending on the types of the samples, a method of pretreating the samples, and/or the like, and can be, for example, 80, 77, 50, 20, 15, or 10.

The marker which can be detected by the marker detecting device 5 is not limited to any particular one, but is preferably a substance which is not contained in the sample. The marker is also preferably the substance which is not decomposed by heat and a reagent which are added between a point of the introduction of the marker into the tube 3 and the marker detecting device 5. For example, the marker can be a substance which can be detected by a spectrophotometer. Such a substance is also not limited to any particular one, and examples thereof include rhodium, nickel, copper, chromium, manganese, iodine, cobalt, nitrate ion, phosphate ion, and silicate ion. Alternatively, the above substance can be a substance which can be detected by a voltammeter. Such a substance is also not limited to any particular one, and examples thereof include copper, cadmium, nickel, mercury, arsenic, and selenium. Alternatively, the above substance can be a substance which can be detected by an ion electrode meter. Such a substance is also not limited to any particular one, and examples thereof include calcium, potassium, fluorine, and ammonia. Alternatively, the above substance can be a substance which can be detected by an ion chromatography. Such a substance is also not limited to any particular one, and examples thereof include ions of inorganic acid and organic acid, phenol, hydrazine, amino acid, and polysaccharides. Alternatively, the above substance can be a substance which can be detected by a turbidimeter. Such a substance is also not limited to any particular one, and examples thereof include silica which is a fine particulate substance that is not dissolved by acid other than hydrofluoric acid. Alternatively, the above substance can be a substance which can be detected by a fluorophotometer. Such a substance is also not limited to any particular one, and examples thereof include benzene, coumarin, and naphthalene. Among these substances, rhodium, cobalt, nickel, copper, and the like are particularly preferable as the marker, from the viewpoint of easiness of detection.

The gas bubble segmenting device 9 is a device for producing, in the tube 3, a plurality of segments that are separated by gas bubbles, by carrying out gas bubble segmentation with respect to the sample and the marker that have been introduced into the tube 3. In an embodiment of the present invention, the gas bubble segmenting device 9 includes a gas introduction tube through which gas is led to the tube 3 and a gas introduction pump which imparts a suction force to the gas introduction tube. By carrying out the gas bubble segmentation, it is possible to suitably mix the reagent and the like, due to a turbulent flow in a segmented liquid which is divided by the gas bubbles. Since the segmented liquid is divided by the gas bubbles and independently flows in the tube 3, it is possible to prevent interdiffusion of the sample. The gas for the gas bubble segmentation is preferably air, but may be an inert gas(es) such as argon and/or helium. Various gases such as nitrogen and oxygen can be also used. Each of these gases may be used solely or two or more of these gases may be used in combination. A method of, in this manner, introducing a reagent into a continuous flow of a sample in a tube which sample is segmented by gas bubbles, carrying out a reaction operation, removing the gas bubbles, and then carrying out an analysis with use of a detector which is provided downstream is referred to as a continuous flow analysis method (CFA).

The reagent adding device 8 is a device for adding the reagent to the flow of the sample that is transferred through the tube 3. The reagent adding device 8 includes a reagent introduction tube through which the reagent is led to the tube 3 and a reagent introduction pump which imparts a suction force to the reagent introduction tube. The reagent can be a reagent which is added during the pretreatment of the sample. The reagent is not limited to any particular one, and examples thereof include: acid such as nitric acid, hydrochloric acid, sulfuric acid, perchloric acid, phosphoric acid, hydrogen peroxide, and hydrofluoric acid; and alkali such as sodium peroxide, calcium carbonate, and sodium carbonate.

The heating device 6 carries out a heat treatment with respect to the sample that is transferred through the tube 3. The heating device 6 can be a thermostatic bath which includes a heater. Note, however, that a configuration of the heating device 6 is not limited to such a configuration, and the heating device 6 can be an ultrasonic decomposing device, a microwave, an autoclave decomposing device, or the like. In the heating device 6, the tube 3 forms a coil or a helix. In an embodiment of the present invention, the heating device 6 is provided downstream of the reagent adding device 8. By heating the sample to which the reagent has been added, it is possible to promote a reaction between the sample and the reagent and thereby pretreat the sample. In the heating device 6, it is possible to carry out, for example, thermolysis or high-temperature and high-pressure decomposition of the sample. In an example illustrated in FIG. 1, the flow analyzer includes a pretreatment unit 7 which is constituted by a single reagent adding device 8 and a single heating device 6. Note, however, that, the flow analyzer may include, instead of the single reagent adding device 8, a plurality of reagent adding devices 8 so that a plurality of reagents are added. Further, in the example illustrated in FIG. 1, the flow analyzer includes a single pretreatment unit 7. Note, however, that the flow analyzer may include a plurality of pretreatment units 7, and in this case, each of the plurality of pretreatment units 7 may include a different number of reagent adding devices 8. In a case where the flow analyzer includes a plurality of pretreatment units 7, it is possible to carry out a pretreatment which involves, for example, carrying out acidolysis under heating, adding acid again, and then carrying out acidolysis under heating. In a case where the flow analyzer includes a plurality of reagent adding devices 8, reagents which are added by the respective plurality of reagent adding devices 8 may be identical to or different from each other.

In the example illustrated in FIG. 1, the reagent adding device 8 is provided downstream of the gas bubble segmenting device 9. Note, however, that disposition of the reagent adding device 8 is not limited such disposition. The reagent adding device 8 may be provided upstream of the gas bubble segmenting device 9. Alternatively, since there is also a case where the reagent which is introduced by the reagent adding device 8 is a reagent for causing the marker to be detected (e.g. coloring liquid), the reagent adding device 8 may be provided, in such a case, downstream of the heating device 6. Alternatively, one or more reagent adding devices 8 each of which is for introducing the reagent that is used in the pretreatment may be provided upstream of the heating device 6, and one or more reagent adding devices 8 each of which is for introducing the reagent that is used to cause the marker to be detected may be provided downstream of the heating device 6.

The analyzing device 4 is a device which analyzes the sample with respect to which the heat treatment has been carried out. In an embodiment of the present invention, the analyzing device 4 is an inductively coupled plasma optical emission spectrometer. Note, however, that the analyzing device 4 is not limited to such an analyzing device, and may be any analyzing device. For example, the analyzing device 4 may be an atomic absorption photometer, an inductively coupled plasma mass spectrometer, an inductively coupled plasma triple quadrupole mass spectrometer, an ion electrode meter, or a spectrophotometer. Note also that the analyzing device 4 is not limited to a device for detecting the presence or absence of a metal element or measuring the concentration of the metal element, and also a measurement target is not limited to any particular one. Note also that the analysis is not limited to a quantitative analysis or a qualitative analysis.

Between the heating device 6 and the analyzing device 4, the marker detecting device 5 is connected to a branch tube which is for extracting, from the tube 3, the sample and the marker which sequentially flow through the tube 3. In other words, the tube 3 branches into two at a stage after the end of the pretreatment of the sample and prior to introduction of the sample into the analyzing device 4, and one (referred to as "tube 3" even after the branching) is connected to the analyzing device 4 while the other (referred to as "branch tube") is connected to the marker detecting device 5. The marker detecting device 5 continuously measures the liquid extracted from the tube 3 through the branch tube. When the marker detecting device 5 detects the marker, the marker detecting device 5 outputs the detection signal to the analyzing device 4. Then, in an embodiment of the present invention, upon receipt of the detection signal, the analyzing device 4 starts acquiring the analysis data. In an embodiment of the present invention, the marker detecting device 5 is a spectrophotometer. In a case where the marker contains rhodium, the marker detecting device 5 outputs, to the analyzing device 4, the detection signal when the marker detecting device 5 detects the rhodium. Note, however, that the marker detecting device 5 is not limited to the spectrophotometer, and can be, for example, a voltammeter, an ion electrode meter, an ion chromatograph, a turbidimeter, or a fluorophotometer. The marker and the sample which sequentially flow are introduced into the analyzing device 4 and the marker detecting device 5, at the same timing, through the tube 3 and the branch tube, respectively. Alternatively, the marker and the sample which sequentially flow may be introduced into the analyzing device 4 and the marker detecting device 5 at different timings, not at the same timing. In a case where the marker and the sample which sequentially flow are introduced into the analyzing device 4 and the marker detecting device 5 at different timings, the marker and the sample need to be introduced into the marker detecting device 5 at a timing earlier than a timing at which they are introduced into the analyzing device 4. In the above embodiment, the analyzing device 4 is configured to start acquiring the analysis data upon receipt of the detection signal. Note, however, that the analyzing device 4 may be configured to start acquiring the analysis data a given time after receipt of the detection signal.

Figure 3:
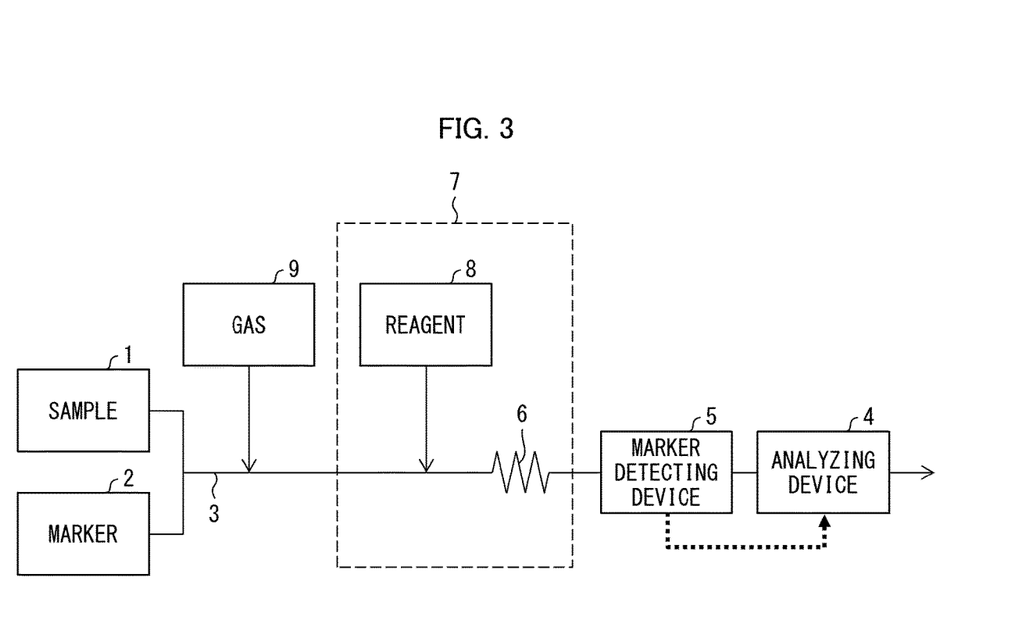
FIG. 3 is a drawing schematically illustrating a configuration of a flow analyzer in accordance with another embodiment of the present invention.

In an embodiment of the present invention, the analyzing device 4 and the marker detecting device 5 are disposed in parallel as stated above. Note, however, that the analyzing device 4 and the marker detecting device 5 may be disposed in series as in an embodiment illustrated in FIG. 3. In the embodiment illustrated in FIG. 3, the marker detecting device 5 is disposed between the heating device 6 and the analyzing device 4. At a stage after the end of the pretreatment of the sample and prior to the introduction of the sample into the analyzing device 4, the marker detecting device 5 continuously measures the liquid that is introduced therethrough the tube 3, and outputs the detection signal to the analyzing device 4 when the marker detecting device 5 detects the marker. Then, after receipt of the detection signal, the analyzing device 4 start acquiring the analysis data. In this case, it is only necessary to adjust a timing of a start of the acquisition of the analysis data so that the analyzing device 4 can measure the sample which has reached the analyzing device 4. For example, the analyzing device 4 may be configured to start acquiring the analysis data a given time after receipt of the detection signal.

According to the flow analyzer in accordance with Embodiment 1, it is possible to continuously introduce the sample into the tube 3, carrying out the gas bubble segmentation, introduce the reagent into the tube 3, promote the reaction with use of the heating device, and then continuously acquire the analysis data with use of the analyzing device. Further, since the flow analyzer includes the marker introducing device which is for introducing the marker into the tube; and the marker detecting device which detects the marker and outputs the detection signal to the analyzing device and the analyzing device acquires the analysis data on the basis of the detection signal, it is possible to stably and continuously measure the sample.

In the above embodiment, the flow analyzer includes the reagent adding device 8 and the heating device 6. Note, however, that the flow analyzer does not necessarily include the reagent adding device 8 and the heating device 6, and may be configured not to include any of the reagent adding device 8 and the heating device 6. In a case where the sample which does not need to be pretreated, the sample which has been already pretreated, and the like are analyzed, the flow analyzer may be configured not to include any of the reagent adding device 8 and the heating device 6. Alternatively, the flow analyzer may be configured to include only the heating device 6 but not to include the reagent adding device 8. On the contrary, the flow analyzer may be configured to include only the reagent adding device 8 but not to include the heating device 6. For example, in a case where the sample to which the reagent such as acid and/or alkali has been added is introduced into the tube 3 and in a case where the heating is needed in the pretreatment but the reagent is not needed, the flow analyzer may be configured to include only the heating device 6 but not to include the reagent adding device 8. In which manner the flow analyzer should be configured can be determined, as appropriate, depending on the method of pretreating the sample.

In an embodiment in which the flow analyzer does not include any of the reagent adding device 8 and the heating device 6, the flow analyzer includes the sampling device 1 which is for introducing the sample into the tube and the analyzing device 4 which analyzes the sample that is transferred through the tube, and further includes the marker introducing device 2 which is for introducing the marker into the tube and the marker detecting device 5 which detects the marker and outputs the detection signal to the analyzing device. The analyzing device 4 acquires the analysis data on the basis of the detection signal.

In the example illustrated in FIG. 1, the flow analyzer in accordance with an embodiment of the present invention may further include a pool tank (reservoir) which is provided in the middle of the tube 3. The flow analyzer employs a method of causing the sample to flow through an enclosed space and analyzing the sample. Therefore, there is a case where pressure increases. Even in such a case, since the flow analyzer includes the pool tank, it is possible to relieve the pressure and suitably dispense and take the sample in an amount that is necessary for each step. The pool tank is not limited in particular in terms of its disposition, provided that the pool tank is disposed in the middle of the tube 3. However, the pool tank is disposed preferably downstream of the heating device 6, and more preferably between the heating device 6 (the most downstream heating device 6, in a case where a plurality of heating devices 6 are provided) and the analyzing device 4. As a means for relieving the pressure in the flow analyzer, a debubbler, which discharges appropriate amounts of the air (gas) and the liquid, a pressure reducing valve, or the like can be, for example, provided instead of the pool tank. In a case where the flow analyzer includes the pool tank, the debubbler, the pressure reducing valve, or the like, another gas bubble segmenting device 9 which newly leads gas to the tube 3 may be provided downstream of such a means. The flow analyzer may include a plurality of pool tanks, debubblers, pressure reducing valves, or the like. Further, the flow analyzer may include a plurality of gas bubble segmenting devices 9.

The flow analyzer in accordance with an embodiment of the present invention may include a pressurizing device which applies, from downstream of the heating device 6, pressure against the flow of the sample. The pressurizing device includes, for example, a compressor and a valve. By providing the pressurizing device, it is possible to promote the reaction in the heating device 6, due to suppression of expansion of the gas bubbles in the heating device 6 and a synergistic effect of the heating and the pressurization. The pressure applied by the pressurizing device is not limited to any particular one, and is, for example, not more than 0.14 MPa.

In the flow analyzer in accordance with an embodiment of the present invention, an autosampler can be used as the sampling device 1. Further, an ultrasonic homogenizer or a stirrer may be provided so as to pulverize and/or stir the sample prior to the sampling.

The flow analyzer in accordance with an embodiment of the present invention may further include a diluting device which is provided in the middle of the tube 3. This makes it possible to automatically carry out desired dilution in the flow analyzer, in a case where it is necessary to dilute the sample depending on the concentration of the sample. As such a diluting device, a commercially available automatic diluting device can be suitably used.

In the flow analyzer in accordance with an embodiment of the present invention, a device which pretreats the sample that is not a liquid but a solid and the like and thereby prepares a liquid sample may be provided to the sampling device 1 or provided upstream of the sampling device 1. The flow analyzer is a device which analyzes a liquid sample by a flow analysis method. Thus, it is not possible to measure, as it is, the sample that is not a liquid but a solid and the like. Therefore, by providing the device which pretreats the sample that is not a liquid but a solid and the like and thereby prepares a liquid sample, it is possible to unintermittedly carry out steps from the pretreatment of the sample that is not a liquid but a solid and the like through the analysis. As such a device, a device which fully automatically pretreats the sample that is not a liquid but a solid and the like is preferable. For example, a fully automatic acidolysis pretreating device which fully automatically carries out addition of the reagent, mixing, heating, and dilution in a measuring flask is suitably used.

Embodiment 2

Figure 2:
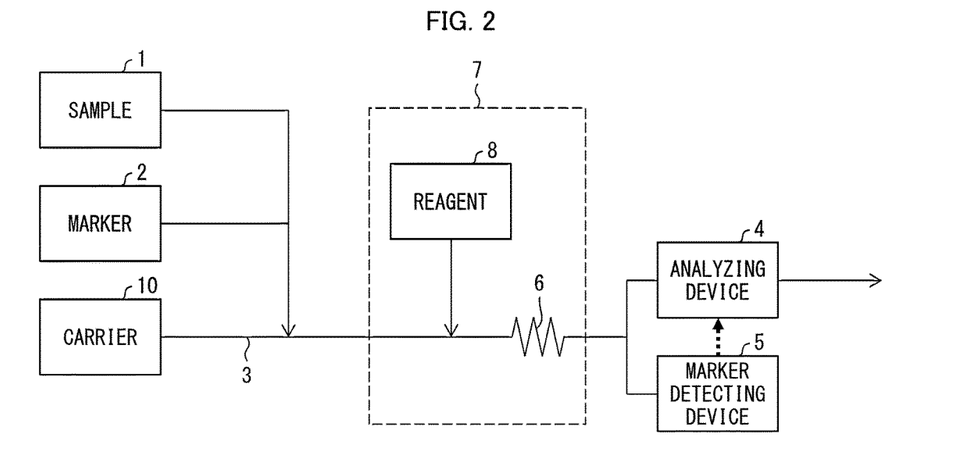
FIG. 2 is a drawing schematically illustrating a configuration of a flow analyzer in accordance with Embodiment 2 of the present invention.

FIG. 2 is a drawing schematically illustrating a configuration of a flow analyzer in accordance with Embodiment 2 of the present invention. Note that, for convenience, members which have the same functions as those of the members that have been described in Embodiment 1 will be given the same reference signs and will not be described again.

A flow analyzer in accordance with Embodiment 2 of the present invention employs a flow injection analysis method (FIA) in which a reagent is introduced into a flow of a sample in a tube which sample is not segmented by gas bubbles, a reaction operation is carried out, and then an analysis is carried out with use of a detector which is provided downstream.

The flow analyzer in accordance with Embodiment 2 of the present invention includes: a carrier introducing device 10 which is for introducing a carrier into a tube 3; a sampling device 1 which is for introducing a sample into the tube 3; a marker introducing device 2 which is for introducing a marker into the tube 3; a reagent adding device 8 which adds a reagent to a flow of the sample that is transferred through the tube 3; a heating device 6 which carries out a heat treatment with respect to the sample that is transferred through the tube 3; an analyzing device 4 which analyzes the sample with respect to which the heat treatment has been carried out; and a marker detecting device 5 which detects the marker and outputs a detection signal to the analyzing device 4, and the analyzing device 4 acquires analysis data on the basis of the detection signal.

The flow analyzer in accordance with Embodiment 2 has the same configuration as that of the flow analyzer illustrated in FIG. 1, except that, in the former, the carrier introducing device 10 is provided upstream of the sampling device 1 which is for introducing the sample into the tube 3 and the marker introducing device 2 which is for introducing the marker into the tube, and a gas bubble segmenting device is not provided.

The flow analyzer in accordance with Embodiment 2 employs the flow injection analysis method (FIA). As such, the carrier introducing device 10 introduces the carrier into the tube 3, and the sampling device 1 and the marker introducing device 2 introduce the sample and the marker, respectively, into the flow of the carrier in the tube 3.

The carrier is not limited to any particular one, provided that the carrier is a liquid which does not adversely affect a pretreatment and the analysis of the sample. Examples thereof include water, surfactants, acid solutions, and alkaline solutions.

The other features of the flow analyzer in accordance with Embodiment 2 are as described in Embodiment 1, and therefore description thereof will be omitted.

(II) Flow Analysis Method

The following description will discuss a flow analysis method in accordance with an embodiment of the present invention. Note that, for convenience, matters which have been already described in (I) Flow analyzer will not be described again.

The flow analysis method in accordance with an embodiment of the present invention includes: a sample introducing step of introducing a sample into a tube; and an analyzing step of analyzing the sample that is transferred through the tube, and further includes a marker introducing step of introducing a marker into the tube between the sample introducing step and a next sample introducing step and a marker detecting step of detecting the marker and outputting a detection signal to an analyzing device. In the analyzing step, analysis data is acquired on the basis of the detection signal.

The sample introducing step is a step of introducing the sample into the tube. For example, a sampling device samples a plurality of samples and sequentially and continuously introduces them into the tube 3 at a given flow rate.

The analyzing step is a step of analyzing the sample that is transferred through the tube. Note, here, that the analysis includes detection of the presence or absence of an analysis target or measurement of the concentration of the analysis target. Note also that the analysis is not limited to a quantitative analysis or a qualitative analysis. Note also that an analysis method is not limited to any particular one, and any analysis can be employed. Examples thereof include atomic absorption photometry, inductively coupled plasma optical emission spectrometry, inductively coupled plasma mass spectrometry, inductively coupled plasma triple quadrupole mass spectrometry, an ion electrode analysis method, and spectrophotometry.

Further, the analysis target is not limited to any particular one, and the method can be, for example, a method for measuring the concentration of a metal element.

The flow analysis method in accordance with an embodiment of the present invention includes the sample introducing step and the analyzing step, and further includes the marker introducing step of introducing the marker into the tube between the sample introducing step and the next sample introducing step. Note, here, that the marker introducing step and the sample introducing step are preferably carried out such that the marker and a given number of samples, which given number is one or more, are alternately introduced into the tube.

Further, the flow analysis method in accordance with an embodiment of the present invention includes the marker detecting step of detecting the marker and outputting the detection signal to the analyzing device, and in the analyzing step, the analysis data is acquired on the basis of the detection signal.

The flow analysis method in accordance with an embodiment of the present invention may be a method in which a continuous flow analysis method (CFA) is used or may be alternatively a method in which a flow injection analysis method (FIA) is used. In a case where the flow analysis method in accordance with an embodiment of the present invention is a method in which the continuous flow analysis method (CFA) is used, the flow analysis method includes a gas bubble segmenting step of producing, in the tube, a plurality of segments that are separated by gas bubbles, by carrying out gas bubble segmentation with respect to the sample and the marker that are introduced into the tube. In a case where the flow analysis method in accordance with an embodiment of the present invention is a method in which the flow injection analysis method (FIA) is used, the flow analysis method can further include a carrier introducing step prior to the sample introducing step and the marker introducing step.

The flow analysis method in accordance with an embodiment of the present invention may further include a heating step of carrying out a heat treatment with respect to the sample that is transferred through the tube. In such a case, the analyzing step is carried out with respect to the sample with respect to which the heat treatment has been carried out. A heating temperature and a heating time in the heating step are not limited to any particular ones, and can be determined, as appropriate, depending on the analysis target, a method of pretreating the sample, and/or the like. The heating temperature is, for example, 25° C. to 150° C. The heating time is, for example, 5 minutes to 1 hour.

The flow analysis method in accordance with an embodiment of the present invention may include a reagent adding step of adding the reagent to the flow of the sample that is transferred through the tube.

INDUSTRIAL APPLICABILITY

According to the present invention, it is possible to stably and continuously carry out, by a flow analysis method, various analyses such as an analysis of metal contained in a solution. Furthermore, since it is possible to carry out a decomposing treatment in a tube, it is possible to reduce contaminants, such as zinc, aluminum, and sodium, which come from outside. Moreover, since a reagent is equally supplied to a sample, it is possible to carry out low-blank measurement by consequently subtracting a blank, even in a case where the reagent contains a contaminant and the like. Therefore, the present invention has extremely high industrial applicability in all of the technical fields in which analyses are carried out.

REFERENCE SIGNS LIST

1 Sampling device
2 Marker introducing device
3 Tube
4 Analyzing device
5 Marker detecting device
6 Heating device
7 Pretreatment unit
8 Reagent adding device
9 Gas bubble segmenting device
10 Carrier introducing device

SUMMARY

Embodiments of the present invention include the following features.

[1] A flow analyzer including: a sampling device which is for introducing a sample into a tube; and an analyzing device which analyzes the sample that is transferred through the tube, the flow analyzer further including: a marker introducing device which is for introducing a marker into the tube; and a marker detecting device which detects the marker and outputs a detection signal to the analyzing device, the analyzing device acquiring analysis data on the basis of the detection signal.

[2] The flow analyzer as described in [1], wherein: the sample includes a plurality of samples; and the marker introducing device and the sampling device are configured such that the marker and, among the plurality of samples, a given number of samples, which given number is one or more, are capable of being alternately introduced into the tube.

[3] The flow analyzer as described in [1] or [2], wherein the analyzing device is an atomic absorption photometer, an inductively coupled plasma optical emission spectrometer, an inductively coupled plasma mass spectrometer, or an inductively coupled plasma triple quadrupole mass spectrometer.

[4] The flow analyzer as described in any one of [1] to [3], the flow analyzer being a device for measuring a concentration of a metal element.

[5] The flow analyzer as described in any one of [1] to [4], the flow analyzer further including a gas bubble segmenting device which produces, in the tube, a plurality of segments that are separated by gas bubbles, by carrying out gas bubble segmentation with respect to the sample and the marker that are introduced into the tube.

[6] The flow analyzer as described in any one of [1] to [5], the flow analyzer further including a heating device which carries out a heat treatment with respect to the sample that is transferred through the tube.

[7] The flow analyzer as described in any one of [1] to [6], the flow analyzer further including a reagent adding device which adds a reagent to a flow of the sample that is transferred through the tube.

[8] A flow analysis method including: a sample introducing step of introducing a sample into a tube; and an analyzing step of analyzing the sample that is transferred through the tube, the flow analysis method further including: a marker introducing step of introducing a marker into the tube between the sample introducing step and a next sample introducing step; and a marker detecting step of detecting the marker and outputting a detection signal to an analyzing device, in the analyzing step, analysis data being acquired on the basis of the detection signal.

[9] The flow analysis method as described in [8], wherein: the sample includes a plurality of samples; and the marker introducing step and the sample introducing step are carried out such that the marker and, among the plurality of samples, a given number of samples, which given number is one or more, are alternately introduced into the tube.

[10] The flow analysis method as described in [8] or [9], wherein in the analyzing step, the sample is analyzed by atomic absorption photometry, inductively coupled plasma optical emission spectrometry, inductively coupled plasma mass spectrometry, or inductively coupled plasma triple quadrupole mass spectrometry.

[11] The flow analysis method as described in any one of [8] to [10], the flow analysis method being a method for measuring a concentration of a metal element.

[12] The flow analysis method as described in any one of [8] to [11], the flow analysis method further including a gas bubble segmenting step of producing, in the tube, a plurality of segments that are separated by gas bubbles, by carrying out gas bubble segmentation with respect to the sample and the marker that are introduced into the tube.

[13] The flow analysis method as described in any one of [8] to [12], the flow analysis method further including a heating step of carrying out a heat treatment with respect to the sample that is transferred through the tube, the sample with respect to which the heat treatment has been carried out being analyzed.

[14] The flow analysis method as described in any one of [8] to [13], the flow analysis method further including a reagent adding step of adding a reagent to a flow of the sample that is transferred through the tube.

EXAMPLES

The present invention will be described in more detail with reference to examples below. Note, however, that the present invention is not limited to the examples, and the present invention also encompasses, in its scope, any example derived by combining, as appropriate, technical means disclosed in differing examples.

Example 1

A flow analysis was carried out by a continuous flow analysis method (CFA) with use of rhodium as a marker. In the flow analysis, it was checked whether the marker was correctly detected.

As a flow analyzer, a flow analyzer which included two pretreatment units (see FIG. 4) was used. Note that the flow analyzer includes: a sampling device 1 which is for introducing a sample into a tube 3; a marker introducing device 2 which is for introducing a marker into the tube 3; gas bubble segmenting devices 9 which each carry out gas bubble segmentation with respect to the sample and the marker that are introduced into the tube 3; reagent adding devices 8 and 8' which add a first reagent and a second reagent, respectively, to a flow of the sample that is transferred through the tube 3; heating devices 6 which each carry out a heat treatment with respect to the sample that is transferred through the tube 3; an analyzing device 4 which analyzes the sample with respect to which the heat treatment has been carried out; and a marker detecting device 5 which detects the marker and outputs a detection signal to the analyzing device 4, and the analyzing device 4 acquires analysis data on the basis of the detection signal. Note also that the flow analyzer includes two pretreatment units, i.e., a first pretreatment unit which includes the reagent adding device 8 that adds the first reagent and the heating device 6 that carries out high-temperature and high-pressure decomposition; and a second pretreatment unit which includes the reagent adding device 8' that adds the second reagent and the heating device 6 that carries out thermolysis. Between the heating device 6 of the first pretreatment unit and the reagent adding device 8' of the second pretreatment unit, a debubbler which discharges an appropriate amount of a liquid is provided, and the gas bubble segmenting device 9 which newly introduces gas into the tube is provided downstream of the debubbler. Between the heating device 6 of the second pretreatment unit and the marker detecting device 5, a debubbler which discharges air is provided, and the gas bubble segmenting device 9 which newly introduces gas into the tube is provided downstream of the debubbler.

Ultrapure water, air, 1 M nitric acid, and a 30% hydrogen peroxide aqueous solution were used as the sample, the gas, the first reagent, and the second reagent, respectively. The rhodium was introduced into the tube as a 2% nitric acid acidic solution (the concentration of the rhodium: 200 mg/L). As the marker detecting device, a spectrophotometer (SCIC4000, manufactured by BL TEC K. K.) was used.

Figure 5:
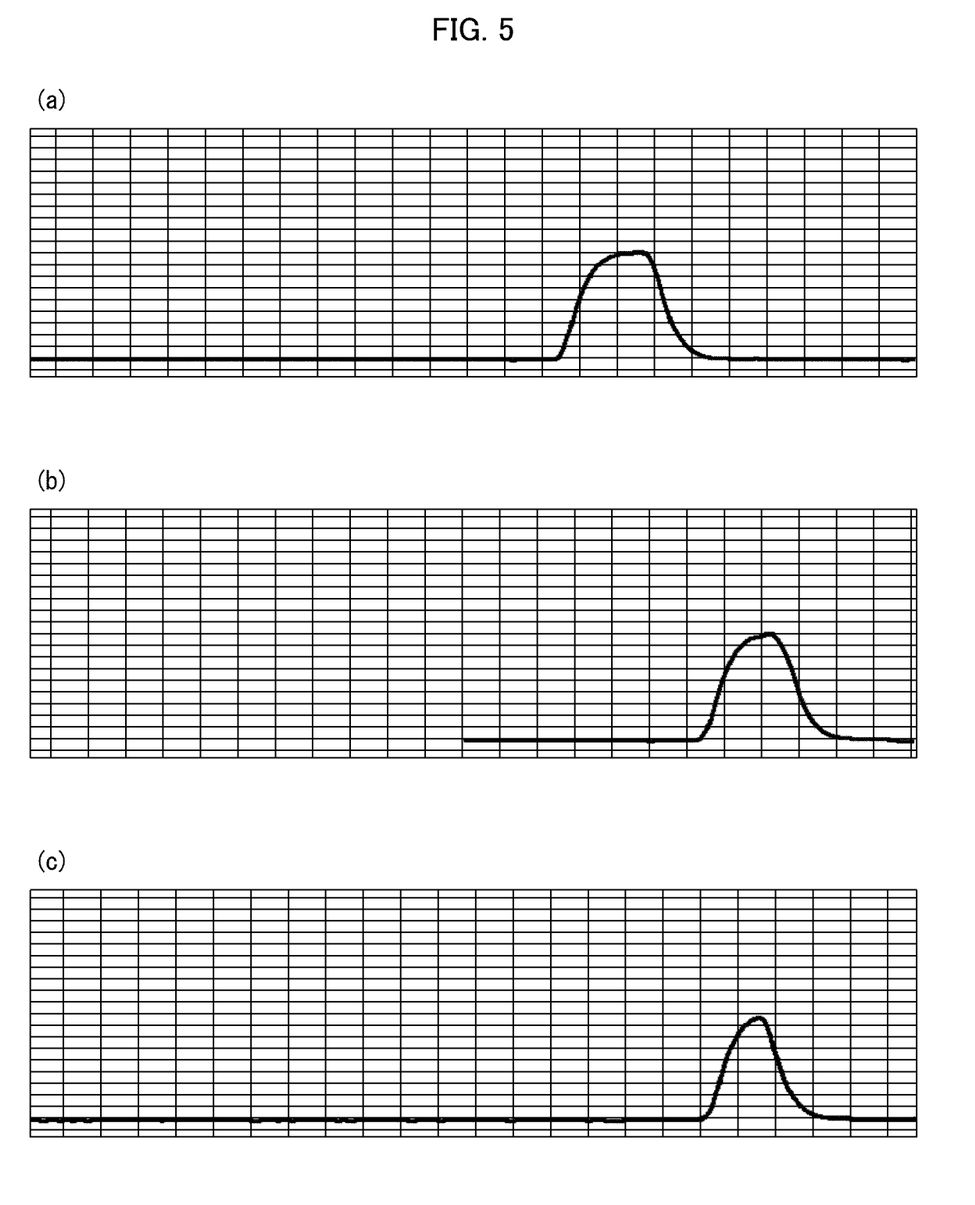
FIG. 5 is a drawing illustrating results of introducing, as a marker, rhodium into a tube and detecting the marker with use of a marker detecting device in Examples of the present invention.

The nitric acid acidic solution of the rhodium and the sample were alternately introduced into the tube. In so doing, 60 seconds, 45 seconds, and 30 seconds were spent in suctioning the nitric acid acidic solution of the rhodium with use of a pump and introducing it into the tube. Then, it was checked whether the rhodium was correctly detected by the marker detecting device 5. FIG. 5 shows results. In FIG. 5, (a), (b), and (c) respectively show temporal variations in absorbance at a wavelength of 405 nm which variations in absorbance were measured by the marker detecting device 5 when 60 seconds, 45 seconds, and 30 seconds were spent in introducing the nitric acid acidic solution of the rhodium into the tube. In FIG. 5, each vertical axis indicates the absorbance, and each horizontal axis indicates a time (one scale unit indicates 30 seconds). As shown in FIG. 5, peaks of the rhodium which had been introduced into the tube were acquired, and it was able to be confirmed that the peaks of the rhodium were correctly detected by the marker detecting device 5. Moreover, it was able to be confirmed that, even when 30 seconds was spend in suctioning the rhodium with use of the pump and introducing it into the tube, the peak of the rhodium was reliably detected.

Example 2

Figure 4:
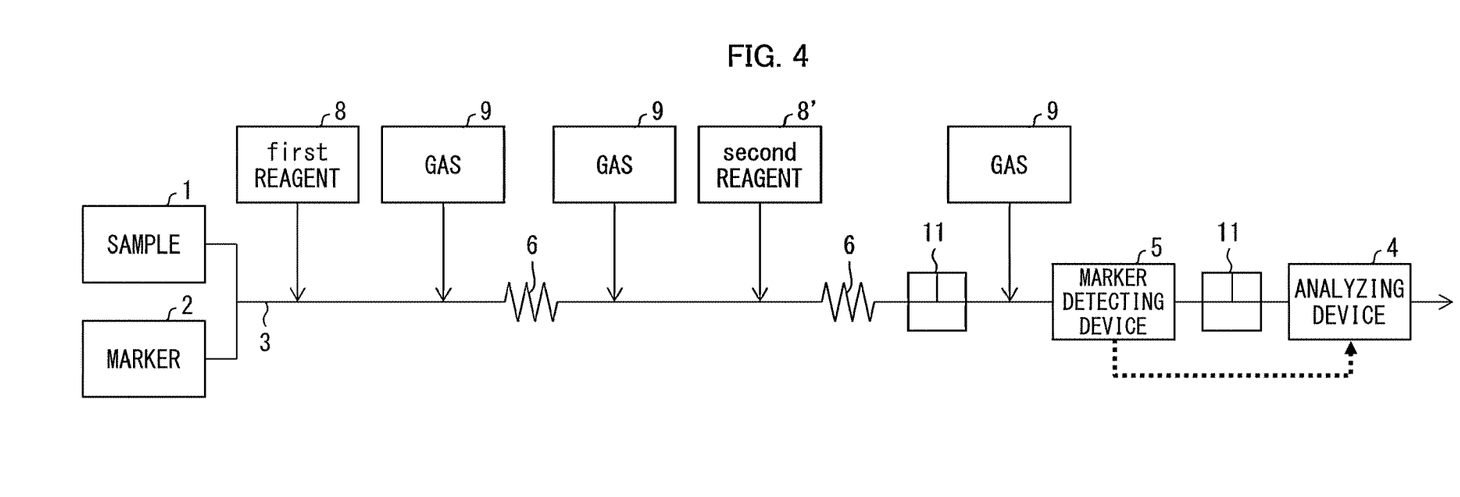
FIG. 4 is a drawing schematically illustrating a configuration of a flow analyzer used in Examples of the present invention.

The same flow analyzer as in Example 1 was used to measure the concentrations of metal elements in samples. As the samples, well water (samples 1 to 7), drinking water (sample 8), and effluent (sample 9) were subjected to the measurement. Air, 1 M nitric acid, and a 30% hydrogen peroxide aqueous solution were used as the gas, the first reagent, and the second reagent, respectively. Rhodium was introduced into the tube as a rhodium(III) nitrate aqueous solution (the concentration of the rhodium: 100 mg/L). As the marker detecting device, a spectrophotometer (SCIC4000, manufactured by BL TEC K. K.) was used. As the analyzing device 4, an inductively coupled plasma mass spectrometer (ICP-MS 7800, manufactured by Agilent Technologies Japan, Ltd.) was used. Calibration curves were each prepared in a concentration range of 0.1 µg/L to 200 µg/L. Table 1 shows measurement results.

Table 1 also shows measurement results obtained by carrying out analyses in accordance with JIS K 0102 (2019) "Testing methods for industrial wastewater", which is a conventional method. The measurement results obtained by the conventional method are shown in a unit of mg/L, and the measurement results obtained in Example 2 are shown in a unit of µg/L. It was able to be confirmed that the measurement results obtained by the conventional method and the measurement results obtained in Example 2 had good correlations therebetween.

TABLE 1

| Sample | | Cd | | Pb | | As | | Se | | Cr | | Zn |
|---|---|---|---|---|---|---|---|---|---|---|---|---|
| | | Conv. | Ex. 2 | Conv. | Ex. 2 | Conv. | Ex. 2 | Conv. | Ex. 2 | Conv. | Ex. 2 | Conv. |
| Well water | Sample 1 | | 0.027 | | 0.108 | | 0.182 | | 0.091 | | 0.135 | Less than 0.005 |

TABLE 1-continued

| | Sample | | | | | | | | | |
|---|---|---|---|---|---|---|---|---|---|---|
| | Sample 2 | 0.028 | | 0.14 | | 4.156 | | 0.034 | 0.063 | 0.009 |
| | Sample 3 | 0.037 | | 22.717 | | 0.122 | | 0.06 | 0.194 | 0.25 |
| | Sample 4 | 0.024 | | 0.105 | | 4.236 | | 0.081 | 0.078 | Less than 0.005 |
| | Sample 5 | 0.032 | | 0.144 | | 2.667 | | 0.176 | 0.103 | Less than 0.005 |
| | Sample 6 | 0.021 | | 0.106 | | 0.964 | | 0.136 | 0.247 | Less than 0.005 |
| | Sample 7 | 0.009 | | 0.208 | | 0.109 | | 0.043 | 0.143 | Less than 0.005 |
| Drinking water | Sample 8 | | | 0.02 | | 0.138 | 0.001 | 1.242 | 0.434 | 0.105 |
| Effluent | Sample 9 | Less than 0.001 | 0.019 | Less than 0.005 | | 0.086 | Less than 0.005 | 1.277 | Less than 0.002 | 0.061 | Less than 0.04 | 0.252 | 0.03 |

| | | Zn | | Fe | | Cu | | Mn | | B | | Al | |
|---|---|---|---|---|---|---|---|---|---|---|---|---|---|
| Sample | | Ex. 2 | Conv. | Ex. 2 | Conv. | Ex. 2 | Conv. | Ex. 2 | Conv. | Ex. 2 | Conv. | Ex. 2 | |
| Well water | Sample 1 | 13.412 | 0.04 | 35.049 | | 0.222 | Less than 0.005 | 7.362 | | 3.326 | | 38.171 | |
| | Sample 2 | 18.677 | 1 | 867.554 | | 0.427 | 0.04 | 38.771 | | 2.533 | | 1.097 | |
| | Sample 3 | 256.076 | 1.4 | 2355.261 | | 285.399 | 0.011 | 11.186 | | 3.875 | | 0.456 | |
| | Sample 4 | 9.917 | Less than 0.01 | 4.229 | | 0.562 | 0.013 | 12.712 | | 15.351 | | 3.111 | |
| | Sample 5 | 3.263 | 0.21 | 204.049 | | 0.363 | 0.023 | 23.043 | | 10.134 | | 17.435 | |
| | Sample 6 | 6.057 | 0.02 | 16.412 | | 0.204 | Less than 0.005 | 1.367 | | 3.775 | | 21.314 | |
| | Sample 7 | 7.976 | 0.11 | 83.365 | | 0.505 | Less than 0.005 | 3.586 | | 3.464 | | 189.366 | |
| Drinking water | Sample 8 | 8.803 | | 5.457 | | 4.91 | Less than 0.005 | 0.455 | | 28.122 | | 2.829 | |
| Effluent | Sample 9 | 28.134 | 0.2 | 18.232 | 0.007 | 5.946 | Less than 0.1 | 9.518 | 0.1 | 98.52 | | 23.38 | |

\* The abbreviation "Conv." stands for "conventional method", and the abbreviation "Ex." stands for "Example".

Example 3

Recovery tests were carried out with use of the same samples as in Example 2, and recovery rates were calculated. Note that a recovery rate is a ratio of an actually measured value to an expected value which is calculated on the basis of a measurement result obtained in Example 2 with respect to a sample, and is obtained with respect to a sample obtained by (i) adding, to 25 mL of the sample, 6.25 mL of a standard solution containing 200 μg/L of a metal element and (ii) diluting the resulting sample to 50 mL in a measuring flask.

The expected value is a set value (target value) of a result of recovery, and is calculated with respect to the metal element in the sample by the following expression.

Expected value(μg/L)=(concentration acquired by measurement in Example 2/2)+25 μg/L The actually measured value indicates a measurement result obtained by measuring, by the same method as in Example 2, the sample which has been diluted to 50 mL in the measuring flask, and is shown in a unit of μg/L.

Tables 2 and 3 show expected values, actually measured values, and the recovery rates of the samples (unit: %). As shown in Tables 2 and 3, good recovery rates were obtained.

TABLE 2

| | | Cd | | | | Pb | |
|---|---|---|---|---|---|---|---|
| Sample | | Actually measured value in Ex. 2 | Expected value | Actually measured value | Recovery rate | Actually measured value in Ex. 2 | Expected value |
| Well water | Sample 1 | 0.027 | 25.0135 | 25.435 | 101.7 | 0.108 | 25.054 |

TABLE 2-continued

| Sample | | | | | | |
|---|---|---|---|---|---|---|
| Well water | Sample 2 | 0.028 | 25.014 | 25.276 | 101 | 0.14 | 25.07 |
| Well water | Sample 3 | 0.037 | 25.0185 | 25.135 | 100.5 | 22.717 | 36.3585 |
| Well water | Sample 4 | 0.024 | 25.012 | 25.505 | 102 | 0.105 | 25.0525 |
| Well water | Sample 5 | 0.032 | 25.016 | 24.819 | 99.21 | 0.144 | 25.072 |
| Well water | Sample 6 | 0.021 | 25.0105 | 26.079 | 104.3 | 0.106 | 25.053 |
| Well water | Sample 7 | 0.009 | 25.0045 | 25.814 | 103.2 | 0.208 | 25.104 |
| Drinking water | Sample 8 | 0.02 | 25.01 | 25.432 | 101.7 | 0.138 | 25.069 |
| Effluent | Sample 9 | 0.019 | 25.0095 | 26.169 | 104.6 | 0.086 | 25.043 |

| | | Pb | | As | | |
|---|---|---|---|---|---|---|
| Sample | | Actually measured value | Recovery rate | Actually measured value in Ex. 2 | Expected value | Actually measured value | Recovery rate |
| Well water | Sample 1 | 25.835 | 103.1 | 0.182 | 25.091 | 25.142 | 100.2 |
| Well water | Sample 2 | 25.392 | 101.3 | 4.156 | 27.078 | 27.104 | 100.1 |
| Well water | Sample 3 | 37.704 | 103.7 | 0.122 | 25.061 | 24.249 | 96.76 |
| Well water | Sample 4 | 25.754 | 102.8 | 4.236 | 27.118 | 27.318 | 100.7 |
| Well water | Sample 5 | 24.996 | 99.7 | 2.667 | 26.3335 | 26.388 | 100.2 |
| Well water | Sample 6 | 25.674 | 102.5 | 0.964 | 25.482 | 26.195 | 102.8 |
| Well water | Sample 7 | 25.493 | 101.5 | 0.109 | 25.0545 | 25.309 | 101 |
| Drinking water | Sample 8 | 25.554 | 101.9 | 1.242 | 25.621 | 25.957 | 101.3 |
| Effluent | Sample 9 | 25.377 | 101.3 | 1.277 | 25.6385 | 26.839 | 104.7 |

| | | Se | | | |
|---|---|---|---|---|---|
| Sample | | Actually measured value in Ex. 2 | Expected value | Actually measured value | Recovery rate |
| Well water | Sample 1 | 0.091 | 25.0455 | 24.55 | 98.02 |
| Well water | Sample 2 | 0.034 | 25.017 | 24.747 | 98.92 |
| Well water | Sample 3 | 0.06 | 25.03 | 24.799 | 99.08 |
| Well water | Sample 4 | 0.081 | 25.0405 | 24.955 | 99.66 |
| Well water | Sample 5 | 0.176 | 25.088 | 24.586 | 98 |
| Well water | Sample 6 | 0.136 | 25.068 | 25.217 | 100.6 |
| Well water | Sample 7 | 0.043 | 25.0215 | 24.681 | 98.64 |
| Drinking water | Sample 8 | 0.434 | 25.217 | 25.456 | 100.9 |
| Effluent | Sample 9 | 0.061 | 25.0305 | 25.576 | 102.2 |

| | | Cr | | | |
|---|---|---|---|---|---|
| Sample | | Actually measured value in Ex. 2 | Expected value | Actually measured value | Recovery rate |
| Well water | Sample 1 | 0.135 | 25.0675 | 24.86 | 99.17 |
| Well water | Sample 2 | 0.063 | 25.0315 | 24.498 | 97.87 |
| Well water | Sample 3 | 0.194 | 25.097 | 24.449 | 97.42 |
| Well water | Sample 4 | 0.078 | 25.039 | 24.822 | 99.13 |

TABLE 2-continued

| | | | | | |
|---|---|---|---|---|---|
| Well water | Sample 5 | 0.103 | 25.0515 | 24.651 | 98.4 |
| Well water | Sample 6 | 0.247 | 25.1235 | 25.305 | 100.7 |
| Well water | Sample 7 | 0.143 | 25.0715 | 25.292 | 100.9 |
| Drinking water | Sample 8 | 0.105 | 25.0525 | 24.506 | 97.82 |
| Effluent | Sample 9 | 0.252 | 25.126 | 25.59 | 101.8 |

* The abbreviation "Ex." stands for "Example".

TABLE 3

| Sample | | Zn | | | | Fe | |
|---|---|---|---|---|---|---|---|
| | | Actually measured value in Ex. 2 | Expected value | Actually measured value | Recovery rate | Actually measured value in Ex. 2 | Expected value |
| Well water | Sample 1 | 13.412 | 31.706 | 26.263 | 82.83 | 35.049 | 42.5245 |
| Well water | Sample 2 | 18.677 | 34.3385 | 29.115 | 84.79 | 867.554 | 458.777 |
| Well water | Sample 3 | 256.076 | 153.038 | 147.263 | 96.23 | 2355.261 | 1202.6305 |
| Well water | Sample 4 | 9.917 | 29.9585 | 26.58 | 88.72 | 4.229 | 27.1145 |
| Well water | Sample 5 | 3.263 | 26.6315 | 25.307 | 95.03 | 204.047 | 127.0235 |
| Well water | Sample 6 | 6.057 | 28.0285 | 25.39 | 90.59 | 16.412 | 33.206 |
| Well water | Sample 7 | 7.976 | 28.988 | 27.134 | 93.6 | 83.365 | 66.6825 |
| Drinking water | Sample 8 | 8.803 | 29.4015 | 26.973 | 91.74 | 5.457 | 27.7285 |
| Effluent | Sample 9 | 28.134 | 39.067 | 39.302 | 100.6 | 18.232 | 34.116 |

| Sample | | Fe | | Cu | | | |
|---|---|---|---|---|---|---|---|
| | | Actually measured value | Recovery rate | Actually measured value in Ex. 2 | Expected value | Actually measured value | Recovery rate |
| Well water | Sample 1 | 42.44 | 99.8 | 0.222 | 25.111 | 25.045 | 99.74 |
| Well water | Sample 2 | 470.479 | 102.6 | 0.427 | 25.2135 | 24.884 | 98.69 |
| Well water | Sample 3 | 1232.877 | 102.5 | 285.399 | 167.6995 | 177.049 | 105.6 |
| Well water | Sample 4 | 27 | 99.58 | 0.562 | 25.281 | 25.123 | 99.38 |
| Well water | Sample 5 | 128.776 | 101.4 | 0.363 | 25.1815 | 24.475 | 97.19 |
| Well water | Sample 6 | 33.234 | 100.1 | 0.204 | 25.102 | 25.386 | 101.1 |
| Well water | Sample 7 | 58.918 | 88.36 | 0.505 | 25.2525 | 25.645 | 101.6 |
| Drinking water | Sample 8 | 25.312 | 91.29 | 4.91 | 27.455 | 27.317 | 99.5 |
| Effluent | Sample 9 | 32.242 | 94.51 | 5.946 | 27.973 | 27.888 | 99.7 |

| Sample | | Mn | | | | B | |
|---|---|---|---|---|---|---|---|
| | | Actually measured value in Ex. 2 | Expected value | Actually measured value | Recovery rate | Actually measured value in Ex. 2 | Expected value |
| Well water | Sample 1 | 7.362 | 28.681 | 26.796 | 93.43 | 3.326 | 26.663 |
| Well water | Sample 2 | 38.771 | 44.3855 | 43.64 | 98.32 | 2.533 | 26.2665 |
| Well water | Sample 3 | 11.186 | 30.593 | 29.354 | 95.95 | 3.875 | 26.9375 |
| Well water | Sample 4 | 12.712 | 31.356 | 30.588 | 97.55 | 15.351 | 32.6755 |

TABLE 3-continued

| | | | | | | | |
|---|---|---|---|---|---|---|---|
| Well water | Sample 5 | 23.043 | 36.5215 | 35.481 | 97.15 | 10.134 | 30.067 |
| Well water | Sample 6 | 1.367 | 25.6835 | 25.34 | 98.66 | 3.775 | 26.8875 |
| Well water | Sample 7 | 3.586 | 26.793 | 26.593 | 99.25 | 3.464 | 26.732 |
| Drinking water | Sample 8 | 0.455 | 25.2275 | 24.256 | 96.15 | 28.122 | 39.061 |
| Effluent | Sample 9 | 9.518 | 29.759 | 29.246 | 98.28 | 98.52 | 74.26 |

| | B | | Al | | | |
|---|---|---|---|---|---|---|
| Sample | Actually measured value | Recovery rate | Actually measured value in Ex. 2 | Expected value | Actually measured value | Recovery rate |
| Well water Sample 1 | 27.349 | 102.6 | 38.171 | 44.0855 | 46.141 | 104.7 |
| Well water Sample 2 | 26.407 | 100.5 | 1.097 | 25.5485 | 26.455 | 103.5 |
| Well water Sample 3 | 27.814 | 103.3 | 0.456 | 25.228 | 25.638 | 101.6 |
| Well water Sample 4 | 33.367 | 102.1 | 3.111 | 26.5555 | 26.145 | 98.45 |
| Well water Sample 5 | 30.862 | 102.6 | 17.435 | 33.7175 | 33.501 | 99.36 |
| Well water Sample 6 | 27.344 | 101.7 | 21.314 | 35.657 | 37.633 | 105.5 |
| Well water Sample 7 | 27.853 | 104.2 | 189.366 | 119.683 | 111.487 | 93.15 |
| Drinking water Sample 8 | 39.193 | 100.3 | 2.829 | 26.4145 | 24.56 | 92.98 |
| Effluent Sample 9 | 71.84 | 96.74 | 23.38 | 36.69 | 37.476 | 102.1 |

* The abbreviation "Ex." stands for "Example".

The invention claimed is:

1. A flow analyzer comprising:
a sampling device having a sampling device thief tube,
an analyzing device,
a marker introducing device having a marker introducing device thief tube, and
a marker detecting device;
wherein the sampling device is configured to introduce a sample into and through a tube via the sampling device thief tube;
wherein the analyzing device is configured to analyze the sample transferred through the tube via the sampling device;
wherein the marker introducing device is configured to introduce a marker into the tube via the marker introducing device thief tube;
wherein the sample includes a plurality of samples, and the marker introducing device and the sampling device are configured such that the marker and, among the plurality of samples, a given number of samples, which given number is one or more, are capable of being alternately introduced into the tube; the introduction of the marker into the tube by the marker introducing device and the introduction of the given number of samples into the tube by the sampling device being automatically and alternately switched therebetween;
wherein at a stage prior to introduction, into the analyzing device, of the marker and the given number of samples which sequentially flow through the tube, the marker detecting device continuously measures liquid flowing through the tube, and outputs a detection signal to the analyzing device when the marker detecting device detects the marker;
wherein the marker detecting device is configured to detect the marker introduced into the tube via the marker introducing device;
wherein the marker detecting device is configured to detect the marker and to output a detection signal to the analyzing device;
wherein the analyzing device is configured to acquire analysis data of the given number of samples when the analyzing device receives the detection signal.

2. The flow analyzer as set forth in claim 1, wherein the analyzing device is an atomic absorption photometer, an inductively coupled plasma optical emission spectrometer, an inductively coupled plasma mass spectrometer, or an inductively coupled plasma triple quadrupole mass spectrometer.

3. The flow analyzer as set forth in claim 1, said flow analyzer being a device for measuring a concentration of a metal element.

4. The flow analyzer as set forth in claim 1, said flow analyzer further comprising
a gas bubble segmenting device which produces, in the tube, a plurality of segments that are separated by gas bubbles, by carrying out gas bubble segmentation with respect to the sample and the marker that are introduced into the tube.

5. The flow analyzer as set forth in claim 1, said flow analyzer further comprising
a heating device which carries out a heat treatment with respect to the sample that is transferred through the tube.

6. The flow analyzer as set forth in claim 1, said flow analyzer further comprising
a reagent adding device which adds a reagent to a flow of the sample that is transferred through the tube.

7. A flow analysis method comprising:
a sample introducing step of introducing a sample into a tube;
a marker introducing step of introducing a marker into the tube between the sample introducing step and a next sample introducing step;
a marker detecting step of detecting the marker and outputting a detection signal to an analyzing device;
wherein the sample includes a plurality of samples, and the marker introducing step and the sampling introducing step are carried out such that the marker and, among the plurality of samples, a given number of samples, which given number is one or more, are capable of being alternately introduced into the tube; the introduction of the marker into the tube and the introduction of the given number of samples into the tube being automatically and alternately switched therebetween;
wherein in the marker detecting step, at a stage prior to introduction, into the analyzing device, of the marker and the given number of samples which sequentially flow through the tube, liquid flowing through the tube is continuously measured, and a detection signal is outputted to the analyzing device when the marker is detected; and
an analyzing step of analyzing the sample that is transferred through the tube, wherein the analyzing step comprises acquiring the analysis data of the given number of samples when the detection signal is received.

8. The flow analysis method as set forth in claim 7, wherein in the analyzing step, the sample is analyzed by atomic absorption photometry, inductively coupled plasma optical emission spectrometry, inductively coupled plasma mass spectrometry, or inductively coupled plasma triple quadrupole mass spectrometry.

9. The flow analysis method as set forth in claim 7, said flow analysis method being a method for measuring a concentration of a metal element.

10. The flow analysis method as set forth in claim 7, said flow analysis method further comprising
a gas bubble segmenting step of producing, in the tube, a plurality of segments that are separated by gas bubbles, by carrying out gas bubble segmentation with respect to the sample and the marker that are introduced into the tube.

11. The flow analysis method as set forth in claim 7, said flow analysis method further comprising
a heating step of carrying out a heat treatment with respect to the sample that is transferred through the tube,
the sample with respect to which the heat treatment has been carried out being analyzed.

12. The flow analysis method as set forth in claim 7, said flow analysis method further comprising
a reagent adding step of adding a reagent to a flow of the sample that is transferred through the tube.

* * * * *